United States Patent

Omura et al.

[11] Patent Number: 5,770,112
[45] Date of Patent: Jun. 23, 1998

[54] OIL-IN-ALCOHOL EMULSIFIED COMPOSITION

[75] Inventors: Takayuki Omura; Teruhiko Hineno; Tomiyuki Nanba; Haruo Ogawa; Kazuaki Suzuki, all of Yokohama, Japan

[73] Assignee: Shiseido Co. Ltd., Tokyo, Japan

[21] Appl. No.: 793,865

[22] PCT Filed: Jul. 12, 1996

[86] PCT No.: PCT/JP96/01939

§ 371 Date: Mar. 11, 1997

§ 102(e) Date: Mar. 11, 1997

[87] PCT Pub. No.: WO97/02888

PCT Pub. Date: Jan. 30, 1997

[30] Foreign Application Priority Data

Jul. 12, 1995 [JP] Japan ..................................... 7-199102

[51] Int. Cl.⁶ .......................... B01J 13/00; A61K 7/075; A61K 7/08; A61K 7/11
[52] U.S. Cl. ..................... 252/308; 424/70.2; 424/70.31; 424/401; 514/937; 514/975
[58] Field of Search ..................................... 252/308, 312; 424/70.31, 401, 70.2; 514/937, 975

[56] References Cited

U.S. PATENT DOCUMENTS

| | | | |
|---|---|---|---|
| 2,463,738 | 3/1949 | Bernhart | 252/308 X |
| 2,702,276 | 2/1955 | Green | 252/308 X |
| 2,990,377 | 6/1961 | May | 252/312 |
| 3,359,212 | 12/1967 | Bailey | 252/312 |
| 4,784,844 | 11/1988 | Thimineur et al. | 424/70.31 X |
| 4,839,167 | 6/1989 | Yamamoto et al. | 424/70.31 X |
| 5,302,382 | 4/1994 | Kasprzak | 424/401 X |

FOREIGN PATENT DOCUMENTS

| | | |
|---|---|---|
| 60-197610 | 10/1985 | Japan . |
| 63-250311 | 10/1988 | Japan . |
| 7-199102 | 10/1997 | Japan . |

*Primary Examiner*—Richard D. Lovering
*Attorney, Agent, or Firm*—Ronald R. Snider

[57] ABSTRACT

The purpose of the present invention is to provide an oil-in-alcohol emulsified composition that the oil phase is uniformly and stably dispersed into an outer phase which is mainly comprised of a lower alcohol.

Accordingly, the oil-in-alcohol emulsified composition of the present invention comprising: (a) an oily component, (b) a lower alcohol, (c) water, and (d) an emulsifier which comprising one or more of polyether-modified silicones represented by the following general formula (1),

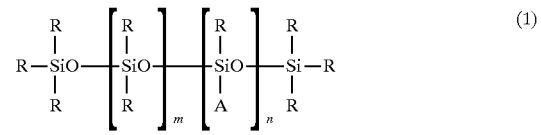

(1)

[In the formula: A is a polyalkylene group shown as the general formula: $-C_3H_6O(C_2H_4O)_a(C_3H_6O)_bR'$ (where R' is a group selected from the group of a hydrogen atom, an acyl group, and alkyl groups having a carbon number of 1 to 4, where a is an integer of 5 to 50, and where b is an integer of 5 to 50.); R is a methyl group or a phenyl group; m is an integer of 50 to 1,000; and n is an integer of 1 to 40.]

4 Claims, No Drawings

OIL-IN-ALCOHOL EMULSIFIED COMPOSITION

This application is a 371 of PCT/JP96/01939 filed on Jul. 12, 1996.

[TECHNICAL FIELD]

The present invention relates to an oil-in-alcohol emulsified composition and in particular, relates to the improvement of its surfactant.

[BACKGROUND ART]

In general, a hair cosmetic preparation is compounded with a large amount of alcohol, in particular ethyl alcohol, as compared with a cosmetic preparation which is applied in other regions. These lower alcohols are worked as a solvent of various ingredients and provide a refresh feeling and disinfectant property in the case where they are applied on hair.

The term hair cosmetic preparation has a significant meaning as a hair dressing function, and polyalkylene glycol which has high alcohol solubility is normally used for giving this hair dressing function.

On the other hand, emulsion type hair cosmetic preparations such as hair cream, have attracted attention from because of the requirements for giving hair gloss, softness, and moisture, and making it easier to comb. Emulsion type hair cosmetic preparations are compounded with an oily component such as silicone oil, liquid paraffin, petrolatum, and the like.

However, it is considerably difficult to make the various oily components disperse and compound uniformly into lower alcohol based compositions.

Namely, the compositions referred to as an emulsified compositions in general, mean the dispersion system of water and oil. For example, in the case of preparing an oil-in-water emulsion, the composition and the amount of the oil phase are determined in first, and then, the type and the amount of the emulsifier which is suitable, and the proper emulsifying process are selected.

In the selection of this emulsifier, the concept of HLB which is experimentally established by Griffin et al. However, this concept of HLB is only related to the solubility of the surfactant in an oil-water system.

And, in general, the HLB of surfactant is prepared in the range of 7 to 18 in an oil-in-water emulsion and 3 to 7 in a water-in-oil emulsion respectively, and emulsification is performed by solubilizing the surfactants into the oil phase or the water phase.

In order to obtain a stable emulsion with a nonionic surfactant which chemically stable and which has a small possibility to degenerate other ingredients, it is necessary to combine a hydrophilic nonionic surfactant and a lipophilic nonionic surfactant. And further, it is necessary to arrange said surfactant to a boundary by enlarging the boundary area between the oil phase and the water phase by the using strong stirring power of a homogenizer and the like. In case of using a specific type of surfactant and further compounding the surfactant in a large amount, the stable emulsion can be obtained without using the above-mentioned process. However, in rare occasions, an allergic reaction is observed in some people. So, in the case where the surfactant is used in the above-mentioned cosmetic preparations, it is necessary to select carefully the type and the amount of the surfactant added.

And, in the case where the hydrophilic property of the hydrophilic nonionic surfactant is in extremely high (HLB is more than about 20), the ability of surface activity is decreased. So, even in the case where a hydrophilic nonionic surfactant is compounded with a lipophilic nonionic surfactant, it is difficult to obtain a stable emulsion.

And further, in reference to the stability of the emulsion, the emulsion which is prepared by the conventional emulsifying process, is not so much favorable in the stability at a high temperatures in general, since the cloudy point of the nonionic surfactant used is relative low.

And, in an oil-in-alcohol emulsified composition which comprises an excessively large amount of alcohol with respect to an amount of water in an outer phase, the evaluation of the surfactant by means of HLB mentioned above is difficult, and the stable emulsion system has not been obtained so far.

For example, Japanese Unexamined Patent Publication No. Sho 60-197610 and Japanese Unexamined Patent Publication No. Sho 63-250311 discloses examples which are compounded silicone oil into a water phase which comprises 50% by weight or more of ethyl alcohol concentration. However, even in these compositions of prior art, it is necessary to add various humectants, and the ethyl alcohol concentration is limited to 50% by weight or less with respect to the water phase. So, the composition is far from regarding as what is called an alcohol based composition.

[DISCLOSURE OF INVENTION]

In view of the above-mentioned problems of the prior art, an object of the present invention is to provide an oil-in-alcohol emulsified composition where the oil phase is dispersed uniformly and stably into an outer phase which is essentially comprised of a lower alcohol.

As a result of diligent studies of the inventors for attaining the above-mentioned objects, it has been found that an oil-in-alcohol emulsified composition which is excellent in stability can be obtained by using a specific polyether-modified silicone. Accordingly, the present invention has been accomplished.

Namely, an oil-in-alcohol emulsified composition in accordance with the present invention comprising: (a) an oily component; (b) a lower alcohol; (c) water; and (d) an emulsifier which comprising one or more of polyether-modified silicones represented by the following general formula (1),

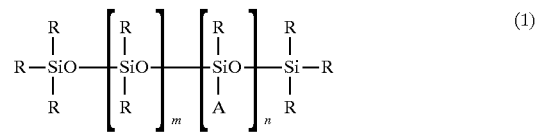

[wherein: A is a polyalkylene group shown as the general formula: —C$_3$H$_6$O(C$_2$H$_4$O)$_a$(C$_3$H$_6$O)$_b$R' (where R' is a group selected from the group of a hydrogen atom, an acyl group, and alkyl groups having a carbon number of 1 to 4, where a is an integer of 5 to 50, and where b is an integer of 5 to 50.); R is a methyl group or a phenyl group; m is an integer of 50 to 1,000; and n is an integer of 1 to 40.].

In said general formula, preferably, R is a methyl group.

In the composition of the present invention, preferably, m is 150 to 1,000.

Also, in the composition of the present invention, preferably, the lower alcohol is comprised three times the amount or more of water.

Preferably, the lower alcohol is comprised 50% by weight or more.

Also, in the present invention, preferably, the compounding ratio of the polyether-modified silicone to the lower alcohol is 1:9 to 5:5 in weight ratio.

Also, preferably, the compositions of the present invention are hair cosmetic preparation.

An oil-in-alcohol emulsified composition in accordance with the present invention is characterized in that the lower alcohol is comprised in an excessive amount with respect to water, in particular, the oil composition is an oil-lower alcohol-water system that the lower alcohol is three times the amount or more of water, and it is characterized in that one or more of polyether-modified silicones shown in the general formula (1) is/are used.

Namely, an emulsified composition of the present invention is entirely different from the conventional emulsification, it is an entirely new oil-in-alcohol emulsified composition which does not use hydrophilic nonionic surfactants, which rather uses the polyether-modified silicone which is gelated by contacting with water as only one emulsifier, and which is emulsified in an oily component at high alcohol concentrations.

In said general formula (1), as for an acyl groups of R', a formyl group, an acetyl group, a propionyl group, a butyryl group, an acryroyl group, a benzoyl group, a toluoyl group, and the like are exemplified. And, as for alkyl groups having a carbon number of 1 to 4, a methyl group, an ethyl group, an i-propyl group, a n-propyl group, a t-butyl group, a n-butyl group, and the like are exemplified.

In the case where a or b is less than 5 in a polyoxyalkylene group, polyether-modified silicone does not show sufficient surface active effect, and in the case where a or b is more than 50, the obtained composition possess a sticky feeling.

The compounding amount of the polyoxyalkylene group in the molecule is not particular limited. It is desirable to compound the polyoxyalkylene group more than 20% by weight with respect to whole amount of the molecule. This is because the thickening effect of the polyether-modified silicone is remarkably decreased, in the case where the compounding amount of a polyoxyalkylene group is 20% by weight or less with respect to the whole amount of the molecule.

Also, m is an integer of 50 to 1,000, and n is an integer of 1 to 40. This is because that the emulsion stability is poor in the case where m is less than 50 and n is less than 1, And this is because the obtained composition has a sticky feeling where m is more than 1,000 and n is more than 40. Preferably, m:n is 200:1 to 5:1, and more preferably 60:1 to 15:1.

The molecular weight of the polyether-modified silicone used in the present invention and its viscosity at 25° C. are not limited in particular. The viscosity in the case of the polyether-modified silicone made with 50% by weight aqueous solution of octamethyl tetrasiloxane or isoparaffin, is desirable to be within the range of 1,000 to 100,000 cps, since the combination forms a particularly stable emulsion and possess a dry feeling.

The compounding amount of the polyether-modified silicone used in the present invention is not limited in particular. Preferably, it is 1% by weight or more, and more preferably, 3% by weight or more. Also preferably, the compounding amount of the polyether-modified silicone is 30% by weight or less, and more preferably, 20% by weight or less. This is because in the case where the compounding amount of the polyether-modified silicone is less than 1% by weight, it is difficult to stably emulsify the composition, and in the case where the compounding amount is more than 30% by weight, the obtained composition possesses a sticky feeling.

The type of the lower alcohol used in the present invention is not limited in particular, and methanol or ethanol is preferable. And in considering the aspects of stability, ethanol is preferable.

Further, i-propanol, n-propanol, t-butanol, s-butanol, and the like are difficult to emulsify, since these ingredients have a strong hydrophobic property. So, these ingredients are desirable to be used together with ethanol.

Preferably, the compounding amount of the lower alcohol is three times the amount or more (weight ratio) with respect to the amount of water in the composition. In the case where the amount of the lower alcohol is less than three times the amount, it is difficult to emulsify the solution because the viscosity is increased since the whole system comes to gelation by the presence of the polyether-modified silicone.

Further, in view of the prior art teaching that is difficult to emulsify oil-in-alcohol systems at high alcohol concentrations, it will be understood the significance of the present invention is where the compounding amount of the lower alcohol is 50% by weight or more with respect to the composition.

The oily components used in the present invention are not limited in particular. The oily components such as liquid paraffin, squalane, lanolin derivatives, higher alcohol, various ester oils, avocado oil, palm oil, beef tallow, jojoba oil, silicone oil, polyalkylene glycol polyether and oligo carboxylate compound, terpene type hydrocarbon oils, and the like are exemplified.

In the oil-in-alcohol emulsified composition of the present invention, in addition to the above-mentioned essential constituents, according to its object, various ingredients may be compounded within the quantity and the quality range as long as the effects of the present invention are not spoiled. Examples of such ingredients include water soluble polyvalent alcohols such as ethylene glycol, propylene glycol, 1,3-butylene glycol, glycerin, sorbitol, polyethylene glycol, and the like; humectants such as hyaluronic acid, chondroitin sulfate, pyrrolidone carboxylate, and the like; UV-absorbent; UV-scattering agent; resins such as acrylic resin, silicone resin, polyvinylpyrrolidone, and the like; proteins or protein decomposition products such as soybean protein, gelatin, collagen, silk fibroin, elastin, and the like, antiseptic agents such as ethyl paraben, butyl paraben and the like, activating agents such as various amino acid, biotin, pantothenic acid derivatives, and the like; blood flow stimulants such as γ-oryzanol, sodium dextran sulfate, vitamin E derivatives, nicotine derivatives and the like; antiseborrheic agents such as sulfur, thiantol, and the like; diluents such as ethanol, isopropanol, tetrachlorodifluoroethane, and the like; thickening agents such as carboxyvinyl polymer; drug; perfume; coloring agent, and the like.

The oil-in-alcohol emulsified composition is used as various hair cosmetic preparations such as general hair dressing preparations, shampoo agents, rinse agents, treatment agents, set agents, permanent waving lotions, mascara, and the like.

And the composition also can be used for alcohol-based external preparations for skin which have a high alcohol concentration, e.g., skin lotion, and the like.

[BEST MODE FOR CARRYING OUT THE INVENTION]

In the following, the preferable embodiments of the present invention are explained.

In the first place, the inventors studied about the emulsion stability in alcohol-based as compared with the following representive oil-in-water type emulsifying process.

Conventional process 1
  (1) Propylene glycol: 2.5
  (2) Polyoxyethylene hydrogenated castor oil (60E.O): 1.0
  (3) Ion-exchanged water: 11.5
  (4) Dimethylpolysiloxane (n=3,000): 15.0
  (5) Ethanol: 70.0
Process
The ingredient (2) and a part of the ingredient (3) were mixed into the ingredient (1), and emulsified by adding the ingredient (4). After this, the ingredient (5) was added.
Conventional process 2
  (1) Ion-exchanged water: 9.6
  (2) Dimethylpolysiloxane (n=3,000): 15.0
  (3) Isostearic acid: 0.4
    (Trade name: ISOSTEARIC ACID PK, produced by KOKYU ALCOHOL CO.,LTD.)
  (4) Imidazolinium betaine amphoteric surfactant: 5.0
    (Trade name: OVAZOLINE 662-N, produced by TOHO KAGAKU K.K.)
  (5) Ethanol: 70.0
Process
Emulsified by adding the ingredients (1), (2), (3), and (4), and then, the ingredient (5) was added.
Conventional process 3
  (1) Dimethylpolysiloxane (n=3,000): 15.0
  (2) Alkyl denatured carboxyvinyl polymer: 0.2
    (Trade name: PEMULEN TR-2, B. F. GOODRICH COMPANY)
  (3) Ion-exchanged water: 14.2
  (4) Potassium hydroxide (10% aqueous solution): 0.6
  (5) Ethanol: 70.0
Process
A part of the ingredient (3) was added to the mixture of the ingredients (1) and (2), and then, emulsified by adding the ingredient (4). After this, the rest of the ingredient (3) was added, and further the ingredient (5) was added to this.
Conventional process 4 to 6
All amounts of ethanol of said conventional process 1 to 3 were replaced with ion-exchanged water, and emulsifying operation was performed by the same processes as above.
Present emulsifying process
  (1) Dimethylpolysiloxane (n=3,000): 15.0
  (2) Polyether-modified silicone (Note 1): 5.0
  (3) Ion-exchanged water: 10.0
  (4) Ethanol: 70.0
Process
Emulsifying the rest of the ingredient (4) under stirring with the ingredients (1), (2), and a part of the ingredients (3) and (4), after then adding the rest of the ingredient (3).

TABLE 1

| Emulsifying process | Stability |
|---|---|
| Conventional process 1 | Δ (creaming in a moment, and then demulsified) |
| Conventional process 2 | × (demulsified in a moment) |
| Conventional process 3 | □ (aggregated in a moment) |
| Conventional process 4 | ○ |
| Conventional process 5 | ○ |
| Conventional process 6 | ○ |
| Present emulsifying process | ○ (stable (at 50° C., in 3 months)) |

In Table 1, conventional process 1 used propylene glycol which has high solubility with respect to ethanol. However, polyoxyethylene hydrogenated castor oil (surfactant) did not show a preferable emulsion state by the reason that dimethylpolysiloxane was compounded as an oily component, was creaming in a moment, and then it demulsified.

On the other hand, even though conventional process 2 used imidazolinium betaine amphoteric surfactant as general surfactant, it did not obtain any emulsifying action.

Further, in conventional process 3, an attempt was made to prepare a stable dispersion system by thickening the emulsified composition with no common emulsifier, other than alkyl denatured carboxyvinyl polymer and potassium hydroxide. However, the aggregation occurred in this case, and the proper emulsified composition was not obtained.

On the other hand, in the case where all amounts of ethanol were replaced with ion-exchanged water (conventional process 4 to 6) in correspondence with said conventional process 1 to 3, emulsion stability in some degree was obtained. As a result of this, it was found that ethanol gives an extremely bad influence on emulsion stability.

On the other hand, when the emulsifying process of the present invention was used the polyether-modified silicone as an emulsifier, even in the case where a large amount (70% by weight) of ethanol was compounded, the extremely stable emulsifying state was obtained.

And, the inventors paid attention to the emulsion stability giving effect of the polyether-modified silicone in an ethanol-based emulsified composition, and they further conducted the following tests.

Selection of Polyether-Modified Silicone

Namely, the comparison of the emulsifying ability of the polyether-modified silicone of the present invention and other polyether-modified silicones in Tables 2 to 5 will be shown.

Process of Each Composition

Any of the ingredients (1), (2), and (3) were mixed. The ingredients (4) and (5) were further added to this and stirred, after then emulsified by adding the ingredient (6).

(Note 1)

$$CH_3-SiO\begin{pmatrix}CH_3\\|\\CH_3\end{pmatrix}\begin{pmatrix}CH_3\\|\\SiO\\|\\CH_3\end{pmatrix}_{400}\begin{pmatrix}CH_3\\|\\SiO\\|\\(CH_2)_3O(C_2H_4O)_{24}(C_3H_6O)_{24}H\end{pmatrix}_{10}SiCH_3\begin{pmatrix}CH_3\\|\\\\|\\CH_3\end{pmatrix}$$

50% solution of isoparaffin

TABLE 2

Basic formulation

| | |
|---|---|
| (1)Dimethylpolysiloxane 6CS | 24 |
| (2)Dimethylpolysiloxane (n = 3,000) | 24 |
| (3)Polyester-modified silicone (Note 2) | 10 |
| (4)Ion-exchanged water | 1 |
| (5)Ethanol (95%) | 1 |
| (6)Ethanol (95%) | 40 |

Note 2

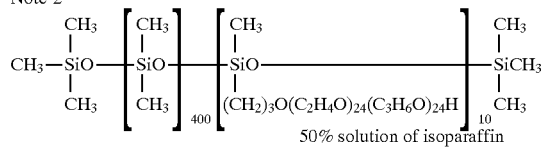

50% solution of isoparaffin

The following Table 3 shows the test results of emulsion stability and stickiness in the case where the value of m, n, and b were fixed at 400, 10, and 24 respectively and the value of a was changed in the general formula (2) of Table 2 above.

TABLE 3

| Test example | 1 | 2 | 3 | 4 | 5 |
|---|---|---|---|---|---|
| Polyether-modified silicone | | | | | |
| m | 400 | 400 | 400 | 400 | 400 |
| n | 10 | 10 | 10 | 10 | 10 |
| a | 3 | 5 | 24 | 47 | 60 |
| b | 24 | 24 | 24 | 24 | 24 |
| Emulsion stability | x○ | ○ | ○ | ○ | |
| Stickiness | ○ | ○ | ○ | ○ | Δ |

As is clear from Table 3, that emulsion stability was unfavorable in the case where the value of a was 3. However, in the case where the value of a was 5 to about 50, it showed favorable results in emulsion stability and stickiness. And in the case where the value of a was 60, it had no big effect in emulsion stability. However, the obtained emulsified composition was not preferable, because the emulsion caused stickiness. As a result of this, it is understood that the value of a is preferably 5 to 50.

And, in the case where the value of b was changed instead of the value of a in the above-described test, almost same results were shown.

The following Table 4 shows the test results of emulsion stability and stickiness in the case where the value of n, a, and b were fixed at 10, 24, and 24 respectively and the value of m was changed in the general formula (2) of Table 2 above.

TABLE 4

| | Test example | | | | | | | | |
|---|---|---|---|---|---|---|---|---|---|
| | 6 | 7 | 8 | 9 | 10 | 11 | 12 | 13 | 14 |
| Polyether-modified silicone | | | | | | | | | |
| m | about 30 | 50 | 120 | 150 | 220 | 400 | 800 | 1000 | 2000 |
| n | 10 | 10 | 10 | 10 | 10 | 10 | 10 | 10 | 10 |
| a | 24 | 24 | 24 | 24 | 24 | 24 | 24 | 24 | 24 |
| b | 24 | 24 | 24 | 24 | 24 | 24 | 24 | 24 | 24 |
| Emulsion stability | x | Δ*1 | Δ*1 | 0 | 0 | 0 | 0 | 0 | Δ |
| Stickiness | ○ | ○ | ○ | ○ | ○ | ○ | ○ | ○ | Δ |

As is clear from Table 4, in the case where the value of m was 30, it remarkably lacked emulsion stability. And, in the case where the value of m was 50, emulsion stability was slightly improved, but the shelf stability at high temperatures was still unfavorable.

On the other hand, in the case where the value of m was 200 or more, it is understood that the emulsion stability together with the shelf stability at high temperatures were largely improved.

Accordingly, it is understood that the value of m is preferably 50 to 1,000 and more preferably 150 to 1,000.

The following Table 5 shows the test results in the case where the value of n was changed in the general formula (2) of Table 2 above.

TABLE 5

| | Test example | | | | | | |
|---|---|---|---|---|---|---|---|
| | 15 | 16 | 17 | 18 | 19 | 20 | 21 |
| Polyether-modified silicone | | | | | | | |
| m | 400 | 400 | 400 | 400 | 400 | 400 | 400 |
| n | 0 | 1 | 3 | 10 | 30 | 40 | 50 |
| a | 24 | 24 | 24 | 24 | 24 | 24 | 24 |
| b | 24 | 24 | 24 | 24 | 24 | 24 | 24 |
| Emulsion stability | x | Δ | ○ | ○ | ○ | ○ | ○ |
| Stickiness | — | ○ | ○ | ○ | ○ | Δ | x |

In Table 5, in the case where the value of n was 0, emulsion stability was hardly observed. However, in the case where the value of n was 1, a slight stabilizing effect was observed, and in the case where the value of n was 3 or more, a more remarkable emulsion stability was obtained.

However, in the case where the value of n was more than 40, it had a tendency to be sticky, and it is understood that the preferable range of n was 1 to 40, and more preferably, 3 to 30.

The Ratio of the Compounding amount of the Lower Alcohol and Water

Next, the test as shown in Table 6 was performed. And, a study about the ratio of the compounding amount of the lower alcohol and water which was preferable in the present invention was performed.

TABLE 6

| Test example | 22 | 23 | 24 | 25 | 26 |
|---|---|---|---|---|---|
| Dimethylpolysiloxane 6CS | 24 | 24 | 24 | 24 | 24 |
| Dimethylpolysiloxane (n = 3,000) | 24 | 24 | 24 | 24 | 24 |
| Polyether silicone (m:400, n:10, a:24, b:24) | 10 | 10 | 10 | 10 | 10 |
| Ion-exchanged water | 1 | 5 | 10 | 20 | 30 |
| Ethanol | 1 | 5 | 10 | 20 | 12 |
| Ethanol | 40 | 32 | 22 | 2 | — |
| Ethanol/water | 41 | 7.4 | 3.2 | 1.1 | 0.4 |
| Emulsion stability | ○ | ○ | ○ | Δ | Δ |

As is clear from Table 6, in the case where ethanol was compounded three times the amount or more (test examples, 22, 23 and 24) of ion-exchanged water, the excellent emulsion stability was obtained. However, in the case where ethanol was compounded within an amount which was equivalent to ion-exchanged water, it became difficult to emulsify since the whole of system made a gelation and the viscosity was increased. Therefore, in the present invention, the compounding amount of the lower alcohol is preferably three times the amount or more of water in composition.

Next, the present invention will be clearly explained by listing the examples and comparative examples. The present invention is not limited to these. The compounding amount is % by weight.

EXAMPLE 1

Hair cream (treatment type)
(1)Dimethylpolysiloxane (n=3,000): 2.0
(2)Light liquid isoparaffin: 30.0
(3)Polyether-modified silicone (Note 3): 15.0
(4)Ethanol: 40.0
(5)Ion-exchanged water: 13.0
(6)Perfume: q.s.
(7)Paraben: q.s.
(8)Antioxidant: q.s.

Process

While stirring a mixture of the ingredients (1), (2), (3), and (5), and a part of the ingredient (4) by a homomixer at room temperature, a mixture of the rest of the ingredient (4) and the ingredients (6), (7), and (8) was added. A hair cream was obtained.

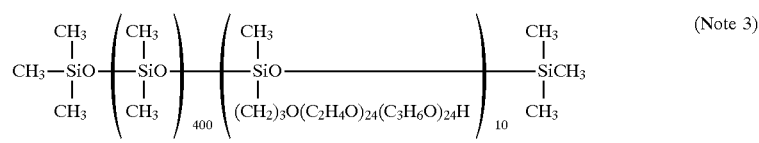

50% solution of isoparaffin

EXAMPLE 2

Hair cream
(1)Amino-modified silicone: 1.0
(2)Dimethylpolysiloxane 6 cs: 3.0
(3)Polyether-modified silicone (Note 3): 10.0
(4)Ethanol: 76.0
(5)Ion-exchanged water: 5.0
(6)Perfume: q.s.
(7)Paraben: q.s.
(8)Antioxidant: q.s.
(9)Polyvinylpyrrolidone/polyvinyl acetate copolymer: 5.0

Process

While stirring a mixture of the ingredients (1), (2), (3), and (5), and a part of the ingredient (4) by a homomixer at room temperature, a mixture of the rest of the ingredient (4) and the ingredients (6), (7), (8), and (9) was added. A hair cream was obtained.

EXAMPLE 3

Treatment mist
(1)Dimethylpolysiloxane 6 cs: 8.0
(2)Dimethylpolysiloxane (n=2,000): 8.0
(3)Ion-exchanged water: 3.0
(4)Ethanol: 75.9
(5)Perfume: q.s.
(6)Octyl methoxycinnamate: 0.1
(7)Polyether-modified silicone (Note 4): 5.0

Process

While stirring a mixture of the ingredients (1), (2), (3), and (7) and a part of the ingredient (4) by a homomixer at room temperature, a mixture of the rest of the ingredient (4) and the ingredients (5) and (6) was added. A treatment mist was obtained.

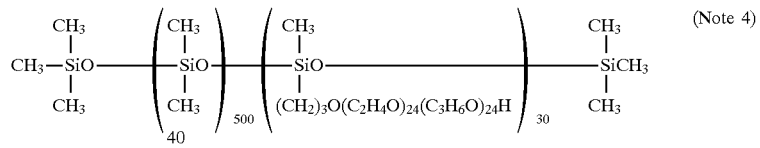

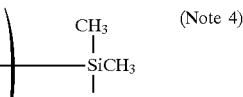
(Note 4)

EXAMPLE 4

Styling mist
(1)Dimethylpolysiloxane 6 cs: 4.0
(2)Dimethylpolysiloxane (n=1,000): 4.0
(3)Ion-exchanged water: 1.0
(4)Ethanol: 75.9
(5)Perfume: q.s.
(6)2-hydroxy-4-methoxybenzophenone: 0.1
(7)Polyether-modified silicone (Note 4): 5.0.
(8)Betain modified dialkylamino alkylacrylate copolymer: 10.0
   (Trade name: YUKAFORMER AM75R205 S, produced by MITSUBISHI CHEMICAL CORP.)

(Note 3)

Process

While stirring a mixture of the ingredients (1), (2), (3), and (7) and a part of the ingredient (4) by a homomixer at room temperature, a mixture of the rest of the ingredient (4) and the ingredients (5) and (6) was added. A styling mist was obtained.

EXAMPLE 5
Treatment lotion
- (1) Dimethylpolysiloxane 20 cs: 15.0
- (2) Dimethylpolysiloxane (n=5,000): 15.0
- (3) Ion-exchanged water: 5.0
- (4) Ethanol: 49.9
- (5) Perfume: q.s.
- (6) Octyl methoxycinnamate: 0.1
- (7) Polyether-modified silicone (Note 2): 15.0

Process

While stirring a mixture of the ingredients (1), (2), (3), and (7) and a part of the ingredient (4) by a homomixer at room temperature, a mixture of the rest of the ingredient (4) and the ingredients (5) and (6) was added. A treatment lotion was obtained.

EXAMPLE 6
Styling lotion
- (1) Dimethylpolysiloxane 6 cs 3.0
- (2) Dimethylpolysiloxane (n=1,000): 3.0
- (3) Ion-exchanged water: 1.0
- (4) Ethanol: 80.9
- (5) Perfume: q.s.
- (6) 2-hydroxy-4-methoxybenzophenone: 0.1
- (7) Polyether-modified silicone (Note 2): 3.0
- (8) Polyvinylpyrrolidone/polyvinyl acetate copolymer: 7.0
- (9) Polyvinylpyrrolidone/dimethylaminoethyl methacrylate copolymer: 2.0

Process

While stirring a mixture of the ingredients (1), (2), (3), and (7) and a part of the ingredient (4) by a homomixer at room temperature, a mixture of the rest of the ingredient (4) and the ingredients (5), (6), (8), and (9) was added. A styling lotion was obtained.

EXAMPLE 7
Treatment mist
- (1) Dimethylpolysiloxane 6 cs: 10.0
- (2) Dimethylpolysiloxane (n=2,000): 10.0
- (3) Ion-exchanged water: 3.0
- (4) Ethanol: 71.9
- (5) Perfume: q.s.
- (6) Octyl methoxycinnamate: 0.1
- (7) Hydrolized woolkeratin (Average molecular weight 1000): 0.1
- (8) Polyether-modified silicone (Note 3): 5.0

Process

While stirring a mixture of the ingredients (1), (2), (3), and (8) and a part of the ingredient (4) by a homomixer at room temperature, a mixture of the rest of the ingredient (4) and the ingredients (5), (6), and (7) was added. A treatment mist was obtained.

COMPARATIVE EXAMPLE 1
Hair cream (treatment type)
- (1) Carrageenan: 1.0
- (2) Polyoxyethylene hydrogenated castor oil (60E.0): 1.0
- (3) Carboxyvinyl polymer: 0.6
  (Trade name: CARBOPOL 940, produced by B. F. GOODRICH COMPANY)
- (4) Dimethylpolysiloxane (n=1,000): 5.0
- (5) Triethanolamine: q.s. (pH7.5)
- (6) Glycerin: 2.0
- (7) Perfume: q.s.
- (8) Octyl methoxycinnamate: 0.1
- (9) Ethanol: 25.0
- (10) Ion-exchanged water: 65.3

Process

The ingredients (2) and (4) were emulsified by adding the ingredient (6) (emulsion parts).

After dissolving uniformly by adding the ingredients (1) and (3) to the ingredient (10), the emulsion parts were mixed into a mixture which was obtained by adding the ingredients (5), (7)–(9). A hair cream treatment was obtained.

COMPARATIVE EXAMPLE 2
Hair cream (treatment type)
- (1) Isoparaffin: 10.0
- (2) Dimethylpolysiloxane: (n=3,000): 5.0
- (3) Diglyceryl diisostearate: 20.0
- (4) Dextrin fatty acid ester: 1.5
- (5) Dimethyl distearyl ammonium hectorite: 1.5
- (6) Ion-exchanged water: 56.4
- (7) Glycerin: 4.0
- (8) Polyethylene glycol 6000: 0.5
- (9) Carboxyvinyl polymer: 0.5
  (Trade name: CARBOPOL 940, produced by B. F. GOODRICH COMPANY)
- (10) Carrageenan: 0.5
- (11) Sodium hydroxide: 0.1

Process

The ingredients (1) to (8) were emulsified by mixing and stirring. Then the ingredients (9) to (11) were added, and a hair cream was obtained.

COMPARATIVE EXAMPLE 3
Treatment mist
- (1) Decamethyl cyclopentasiloxane: 6.0
- (2) Octamethyl cyclotetrasiloxane: 4.0
- (3) Dimethylpolysiloxane (n=1,000): 3.0
- (4) 1,3-Butylene glycol: 3.0
- (5) Polyoxyethylene hydrogenated castor oil (60E.0): 2.0
- (6) Ethanol: 5.0
- (7) Ion-exchanged water: 76.0
- (8) Betain modified dialkylamino alkylacrylate copolymer: 1.0
  (Trade name: YUKAFORMER AH75R205 S, produced by MITSUBISHI CHEMICAL CORP.)
- (9) Perfume: q.s.

Process

The ingredient (3) was dissolved into a mixture of ingredients (1) and (2). The mixture was emulsified by adding a mixture of the ingredients (4) and (5). And then, the ingredients (6), (7), (8), and (9) were mixed into this.

COMPARATIVE EXAMPLE 4
Set lotion
- (1) Polyvinylpyrrolidone/polyvinyl acetate copolymer: 5.0
- (2) Cetyl-2-ethylhexanoate: 1.0

(3) Stearyl trimethyl ammonium chloride: 0.3
(4) Ethanol: 70.0
(5) Ion-exchanged water: 23.7
(6) Perfume: q.s.

Process

The ingredients (4) and (5) were stirred and dissolved. The ingredients (1) to (3), and (6) were further dissolved into this, and set lotion was obtained.

<Evaluation results>

Evaluation of feeling/hair style

After wetting a strand of human hair by water which was uniformly arranged the roots and the top of the hair, 2.0 g of hair set agent composition was applied to the strand and a hair style was finished by 10 beauty experts. Then the organoleptic evaluation was done about (B) less stickiness after applied to drying, (C) smoothness in applying, and (D) smoothness after drying.

The evaluation has been done by finding the average point on the basis of following evaluation point. The test results are shown in Table 7 on the basis of following evaluation results display.

① Evaluation point

+3: Pretty good
+2: Good
+1: Slightly good
0: Normal
−1: Slightly bad
−2: Bad
−3: Extremely bad ② Display of evaluation results XX: Less than −2
X: −2 or more, less than −1
Δ: −1 or more, less than 0
□: 0 or more, less than +1
○: +1 or more, less than +2
◉: +2 or more

TABLE 7

| | Example | | | | | | | Comparative example | | | |
|---|---|---|---|---|---|---|---|---|---|---|---|
| | 1 | 2 | 3 | 4 | 5 | 6 | 7 | 1 | 2 | 3 | 4 |
| Smallness of stickiness | ◉ | ◉ | ◉ | ◉ | ◉ | ◉ | ◉ | Δ | xx | Δ | x |
| Smoothness in applying | ◉ | ◉ | ◉ | ◉ | ◉ | ◉ | ◉ | ○ | Δ | ○ | □ |
| Smoothness after drying | ◉ | ◉ | ◉ | ◉ | ◉ | ◉ | ◉ | Δ | Δ | □ | x |

The oil-in-alcohol hair cosmetic preparation in accordance with the present invention is excellent in emulsion stability and is extremely excellent in feeling of use. It has less stickiness and it can be smoothly applied.

We claim:

1. An oil-in-alcohol emulsified composition comprising:
   (a) an oily component,
   (b) a lower alcohol,
   (c) water, and
   (d) an emulsifier which comprising one or more of polyether-modified silicones represented by the following general formula (1):

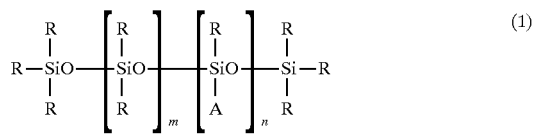

wherein A is a polyalkylene group shown as the general formula: $-C_3H_6O(C_2H_4O)_a(C_3H_6O)_bR'$ (wherein R' is selected from the group consisting of a hydrogen atom, an acyl group, and an alkyl group having a carbon number of 1 to 4, a is an integer of 5 to 50, and b is an integer of 5–50); R is a methyl group or a phenyl group; m is an integer of 150 to 1,000; and n is an integer of 1 to 40.

2. An oil-in-alcohol emulsified composition comprising:
   (a) an oily component,
   (b) a lower alcohol,
   (c) water, wherein the weight ratio of said lower alcohol to water is at least 3:1, and
   (d) an emulsifier which comprising one or more of polyether-modified silicones represented by the following general formula (1):

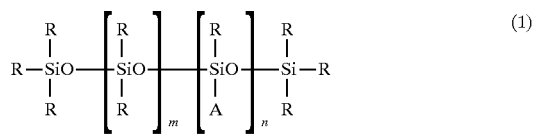

wherein A is a polyalkylene group shown as the general formula: $-C_3H_6O(C_2H_4O)_a(C_3H_6O)_bR'$ (wherein R' is selected from the group consisting of a hydrogen atom, an acyl group, and an alkyl group having a carbon number of 1 to 4, a is an integer of 5 to 50, and b is an integer of 5–50); R is a methyl group or a phenyl group; m is an integer of 50 to 1,000; and n is an integer of 1 to 40.

3. An oil-in-alcohol emulsified composition according to claim 2, wherein the lower alcohol is comprised 50% by weight or more.

4. An oil-in-alcohol emulsified composition comprising:
   (a) an oily component,
   (b) a lower alcohol,
   (c) water, and
   (d) an emulsifier which comprising one or more of polyether-modified silicones represented by the following general formula (1):

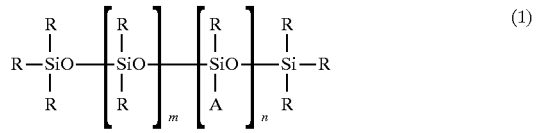

wherein A is a polyalkylene group shown as the general formula: $-C_3H_6O(C_2H_4O)_a(C_3H_6O)_bR'$ (wherein R' is selected from the group consisting of a hydrogen atom, an acyl group, and an alkyl group having a carbon number of 1 to 4, a is an integer of 5 to 50, and b is an integer of 5–50); R is a methyl group or a phenyl group; m is an integer of 50 to 1,000; and n is an integer of 1 to 40, wherein the weight ratio of said polyether-modified silicon to said lower alcohol is 1:9 to 5:5.

* * * * *